US008437001B2

(12) United States Patent
Cheng et al.

(10) Patent No.: US 8,437,001 B2
(45) Date of Patent: May 7, 2013

(54) METHOD FOR FORMING A NANOSTRUCTURE PENETRATING A LAYER

(75) Inventors: Kai Cheng, Leuven (BE); Pol Van Dorpe, Spalbeek (BE); Liesbet Lagae, Leuven (BE); Gustaaf Borghs, Kessel-Lo (BE); Chang Chen, Leuven (BE)

(73) Assignees: IMEC, Leuven (BE); Katholieke Universiteit Leuven, Leuven (BE)

( * ) Notice: Subject to any disclaimer, the term of this patent is extended or adjusted under 35 U.S.C. 154(b) by 0 days.

(21) Appl. No.: 13/157,154

(22) Filed: Jun. 9, 2011

(65) Prior Publication Data

US 2012/0057163 A1 Mar. 8, 2012

Related U.S. Application Data

(63) Continuation of application No. PCT/EP2009/066739, filed on Dec. 9, 2009.

(60) Provisional application No. 61/141,542, filed on Dec. 30, 2008, provisional application No. 61/121,118, filed on Dec. 9, 2008.

(30) Foreign Application Priority Data

Dec. 9, 2008 (EP) ..................................... 08171127

(51) Int. Cl.
*G01N 21/00* (2006.01)

(52) U.S. Cl.
USPC ............................. 356/440; 356/432; 356/441

(58) Field of Classification Search ........................ None
See application file for complete search history.

(56) References Cited

U.S. PATENT DOCUMENTS 6,706,203 B2    3/2004   Barth et al.

FOREIGN PATENT DOCUMENTS

| WO | WO 03/016781 | 2/2003 |
| WO | WO 2005/064634 | 7/2005 |
| WO | WO 2007/054867 | 5/2007 |

OTHER PUBLICATIONS

Hiramatsu et al., Fabrication and characterization of low defect density GaN using facet-controlled epitaxial lateral overgrowth (FACELO), Journal of Crystal Growth, 2000, pp. 316-326.*
Pompa et al, Metal-enhanced fluorescence of colloidal nanocrystals with naoscale control, National Nanotechnology Laboratory of CNR-INFM University of Lecce, Nov. 3 2006, pp. 126-131.*
Li et al., "Ion-beam sculpting at nanometre length scales", Nature, vol. 412, Jul. 2001, pp. 166-169.

(Continued)

*Primary Examiner* — Gregory J Toatley
*Assistant Examiner* — Juan D Valentin, II
(74) *Attorney, Agent, or Firm* — Knobbe Martens Olson & Bear LLP

(57) ABSTRACT

A method for forming a nanostructure penetrating a layer and the device made thereof is disclosed. In one aspect, the device has a substrate, a layer present thereon, and a nanostructure penetrating the layer. The nanostructure defines a nanoscale passageway through which a molecule to be analyzed can pass through. The nanostructure has, in cross-sectional view, a substantially triangular shape. This shape is particularly achieved by growth of an epitaxial layer having crystal facets defining tilted sidewalls of the nanostructure. It is highly suitably for use for optical characterization of molecular structure, particularly with surface plasmon enhanced transmission spectroscopy.

19 Claims, 7 Drawing Sheets

OTHER PUBLICATIONS

Wang et al., "Fabrication of GaN nanowire arrays by confined epitaxy", Applied Physics Letters 89, 233115, 2006.

Ishizawa, et al., "Selective-Area Growth of GaN Nanocolumns on Si (111) Substrates Using Nitrided AI Nanopatterns by RF-Plasma-Assisted Molecular-Bean Epitaxy", Applied Physics Express 1, 015006, 2008.

Hersee et al., "The Controlled Growth of GaN Nanowires", Nano Letters, vol. 6, No. 8, 2006, pp. 1808-1811.

Kneipp et al., "Surface-Enhanced Raman Scattering", Physics and Applications, Topics Appl. Phys. 103, 2006, pp. 45-65.

Hiramatsu, "Epitaxial lateral overgrowth techniques used in group III nitride epitaxy", J. Phys. Condens. Matter, 13, 2001, pp. 6961-6975.

B. Beaumont et al., "Epitaxial Lateral Overgrowth of GaN", Phys. Stat. Sol. (b) 227, No. 1, 2001, pp. 1-43.

Dekker, "Solid-state nanopores", Nature Nanotechnology Nature Publishing Group UK, vol. 2, No. 4, Apr. 2007, pp. 209-215.

Li et al., "Conical Nanopore Membranes. Preparation and Transport Properties", Analytical Chemistry 2004, vol. 76, No. 7, Apr. 2004, pp. 2025-2030.

Deb et al., "Faceted and Vertically Aligned GaN Nanorod Arrays Fabricated without Catalysts or Lithography", Nano Letters, vol. 5, No. 9, Sep. 2005, pp. 1847-1851.

Storm et al., "Fabrication of solid-state nanopores with single-nanometre precision", Nature Materials, Nature Publishing Group, London, vol. 2, No. 8, Jul. 2003, pp. 537-540.

Wang et al., "Nanoscale epitaxial overgrowth process and properties of GaN layers on Si (111) substrates", Applied Physics Letters, AIP, American Institute of Physics, Melville, NY, US, vol. 89, No. 1, Jul. 2006, pp. 011901-1~011901-3.

Wang et al., "Improvement of microstructural and optical properties of GaN layer on sapphire by nanoscale lateral epitaxial overgrowth", Applied Physics Letters, AIP, American Institute of Physics, Melville, NY, US, vol. 88, No. 21, May 2006, pp. 211908-1~211908-3.

M.J. Archer and F.S. Ligler: "Fabrication and Characterization of Silicon Micro-Funnels and Tapered Micro-Channels for Stochastic Sensing Applications", Sensors, vol. 8, Jun. 2008, pp. 3848-3872.

Kim et al., "Transmission characteristics of metallic equilateral triangular nanohole arrays", Applied Physics Letters AIP USA, vol. 89, No. 12, Sep. 2006, pp. 121106-1~121106-3.

International Search Report for International Application No. PCT/EP2009/066739 dated Jun. 17, 2010 by European Patent Office.

Martin Moskovits, "Surface-Enhanced Raman Spectroscopy: a Brief Perspective", Physics and Applications, Topics Appl. Phys. 103, 1-18, (2006).

Rodak et al., "Study of ELOG GaN for Application in the Fabrication of Micro-channels for Optoelectronic Devices", Mater. Res. Soc. Symp. Proc. vol. 892, 2006, Materials Research Society, pp. 0892-FF26-08.1~0892-FF26-08.6.

* cited by examiner

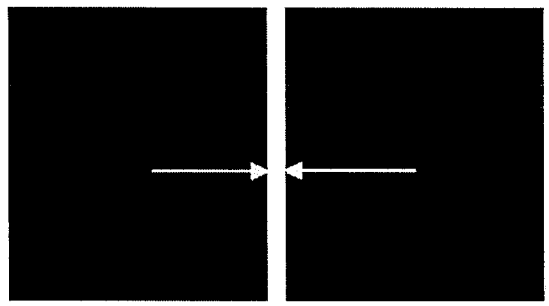
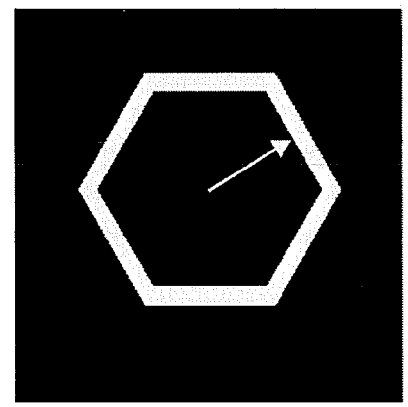
Fig. 5a                Fig. 5B
Fig. 6

METHOD FOR FORMING A NANOSTRUCTURE PENETRATING A LAYER

CROSS REFERENCE TO RELATED APPLICATIONS

This application is a continuation of PCT Application No. PCT/EP2009/066739, filed Dec. 9, 2009, which claims priority under 35 U.S.C. §119(e) to U.S. provisional patent application 61/121,118 filed on Dec. 9, 2008 and to U.S. provisional patent application 61/141,542 filed on Dec. 30, 2008. Each of the above applications is incorporated herein by reference in its entirety.

BACKGROUND OF THE INVENTION

1. Field of the Invention

The disclosed technology relates to a method for forming a nanostructure penetrating a layer, to a device formed therewith, and to use of the device.

2. Description of the Related Technology

Nano-structures have been active for years because of their unique properties in the micro-scale. At the micro-scale, nano-structures-based electrical and optical devices can be integrated with biology, for example single molecule detection and DNA identification. In order to reach such a high resolution, a nano-pore or a nano-slit is always a must.

Numerous ways how to make nano-pores have been described by using electron beams (Storm, A. J. et al. Fabrication of solid-state nanopores with single-nanometre precision. *Nature Mater.* 2, 537-540 (2003)), ion gun (Li, J. et al. Ion-beam sculpting at nanometre length scales. *Nature* 412, 166-169 (2001)) and many other tools. However, the size and the aspect ratio of the nanopore have been limited by the current technology in nanometer scales. Moreover, these nano-structures are always made by etching technology i.e. e-beam, FIB and etc.

In some cases, Nano-structures including nanocolumn and nanowires can be achieved by selective area growth through the pattern in the mask. Some preliminary results have been shown recently (Xin Wang, et al. APL 89, 233115 (2006), S. Ishizawa, et al Applied Physics Express 1, 015006 (2008), S. Hersee, Nano Lett. 6, 1808 (2006). However, very high resolution e-beam lithography has been applied. Furthermore, the feature size of the nano-structures has been limited by the resolution the e-beam lithography.

WO03/16781 discloses a method of analyzing molecules such as DNA, wherein light is directed to a metal surface of a membrane having one or more apertures. The incident light excites surface plasmons (electron density fluctuations) in the top metal surface and this energy couples through the apertures to the opposing surface where it is emitted as light from the apertures or from the rims of the apertures. The extent to which surface plasmons are induced on the surface at the aperture exit may be limited, thereby constraining the resulting emissions to small target areas. The resulting spot illumination may be used to analyze the properties of small objects such as proteins and nucleic acid molecules and single cells.

It is thus desirable to provide a device with an improved signal to noise ratio.

SUMMARY OF CERTAIN INVENTIVE ASPECTS

In a first aspect of the invention, a device is provided that comprises a substrate, a layer present thereon and a nanostructure penetrating the layer, which nanostructure defines a nanoscale passageway through which a molecule to be analyzed can pass through the passageway, wherein the nanostructure has, in cross-sectional view, a substantially triangular shape. More specifically, the layer is an epitaxial layer provided with crystal facets facing the nanostructure.

Such a confinement of the nanostructure defining a restricting channel restriction is for instance highly suitable for applications, in which properties of molecules are detected optically. The confinement both limits the passageway for molecules and simultaneously results in enhancement of a field resulting from electromagnetic radiation directed to the nanostructure. As a result, properties of individual molecules and even segments of individual molecules, such as segments of DNA molecules, for instances individual bases thereof, can be detected.

The nanostructure with a substantially triangular shape in cross-sectional view may be obtained, for instance, by means of etching of a crystalline material and by means of epitaxial growth. In both embodiments, a desired shape with tilted walls may be defined on the basis of a mask. Alignment of the mask with another orientation may give rise to another shape of the resulting etch shape or the resulting growth.

The use of epitaxial growth, and more in particularly epitaxial lateral overgrowth (ELOG) is deemed highly advantageous, as dislocations can be blocked by the mask and the lateral growth region is usually free of dislocations except for a coaslescence boundary. Particularly, during lateral growth, perfect facets can be observed, forming excellent nanostructures. Dimensions of the nanostructures may be further controlled by growth parameters The epitaxial growth using a patterned mask additionally allows formation of specific shapes in addition to the nanostructure. Examples include an access channel to the nanostructure, a ring-shaped nanostructure giving rise to plasmonic resonance upon irradiation in an appropriate manner and chambers with restricted volumes to the passageway. Particularly when using molecules present in a fluid, typically a liquid, in general in a solution, dispersion or other suspension, fluid flow is suitably guided. The chambers defined by facets are appropriate, as such chambers may have tilted walls.

The term "membrane penetrating nanostructure" refers to a space through a membrane. The space may be designed such that a molecule to be analyzed can pass through the space. A membrane penetrating nanostructure should be understood as a structure having a nanoscale passageway through which a molecule can flow. The nanostructure is preferably designed such that the degrees of freedom for the movement of the molecule in the nanostructure is limited to a predefined direction, preferably from one side of the membrane to the other side of the membrane. In one inventive aspect, the movement should be limited to a 1D movement or line movement. The nanostructure is not limited to the region through which the molecule flows, but can be larger such that light can be coupled in the nanostructure. Therefore, the membrane penetrating nanostructure may be, but are not limited hereto, a nanopore, a nanoslit or a nanochannel.

According to a second aspect, an apparatus is provided comprising the device as described herein. Such apparatus is an apparatus for optical transmission spectroscopy. It further comprises a source of electromagnetic radiation that impinges radiation on the nanostructure from a first side, means for translocating molecules through the nanostructure, and a detection unit for detecting electromagnetic radiation that exits from the nanostructure away from a second side opposite to the first side. The transmission of electromagnetic radiation through the nanostructure occurs at least by excitation of surface plasmon polaritons in the nanostructure.

In a third aspect, a method for use is provided. The method is for use with a device comprising a substrate, a patterned epitaxial layer on the substrate, a nanostructure penetrating the epitaxial layer, and an opening through the substrate underlying the nanostructure. Herein, tilted sidewalls of portions of the epitaxial layer face and limit a width of the penetrating nanostructure. This method comprises the steps of getting molecules to flow through the nanostructure, and characterizing the molecules.

In a specific embodiment, light is coupled into the nanostructure from a first side, and the molecules are characterized optically using excitation of surface plasmon wave in the nanostructure. The characterization is based on electromagnetic radiation transmitted through the nanostructure to a second side at least by the excitation.

In a fourth aspect of the present invention, a method for forming a nanostructure penetrating a layer is disclosed. The method comprises a) providing a substrate, b) forming a patterned layer on the substrate, the patterned layer having at least one opening through which the surface of the substrate is exposed, c) growing an epitaxial layer on the substrate, vertically from the opening and laterally across the patterned layer, d) maintaining the lateral growth of the epitaxial layer such that the epitaxial layer is formed over the exposed region of the substrate and such that the epitaxial layer does substantially not coalesce across the patterned layer, and e) removing at least partially the patterned layer in the region where no epitaxial layer is present on the patterned layer such that a nanostructure is formed in the epitaxial layer.

For the purpose of the description, the part of the epitaxial layer where the epitaxial layer does substantially not coalesce across the patterned layer is also called the nanostructure forming part of the epitaxial layer.

In a further aspect of the invention, another device comprising a nanostructure is disclosed. The device comprises a substrate, a piezoelectrical layer present thereon, an electrode operatively associated with the piezoelectric layer and an adjustable nanostructure penetrating the piezoelectrical layer. Herein, the nanostructure having a nanoscale passageway through which a molecule to be analyzed can pass through the passageway and the nanostructure being adjustable by means of application of a voltage on the electrode for deformation of the piezoelectric layer.

When a voltage is applied to the piezoelectric material, the piezoelectric material deforms. When a voltage is applied, an electrically induced mechanical stimulus is applied to the piezoelectric layer, which can deform resulting in a deformation of the membrane penetrating nanostructure. A deformation of the membrane penetrating nanostructure can be, but is not limited hereto, a change of the inner diameter of the membrane penetrating nanostructure. The change can be an increase or decrease of the inner diameter of at least a part of the membrane penetrating nanostructures. Thus, the device may have an adjustable membrane penetrating nanostructure. By applying a predetermined voltage on the piezoelectrical material, the inner diameter of the membrane penetrating nanostructure can set to a predetermined value.

Provision of an adjustable nanostructure is suitable in the context of molecular analysis for several purposes. It could be used for varying the critical dimension of the nanostructure so as to match to specific molecules. In other words, a single device may be tuned for various applications. A more sophisticated use is tuning of the dimensions of the nanostructure so as to improve optical properties. Using surface plasmon resonance, optical properties within the nanostructure are obtained through gap resonance. The resonance frequency may well depend on the wavelength of the light or electromagnetic radiation that is directed to the nanostructure. With certain spectroscopic techniques, such as fluorescence, the wavelength is again coupled to the fluorescent behavior of the molecules, typically fluorescent properties of the label coupled to the molecules. Evidently, resonance may further depend on properties of molecules or segments thereof in the passageway of the nanostructure. In short, the ability of tuning the dimension of the nanostructure, and particularly its portion with smallest dimensions (the passageway), may give rise to larger flexibility and to improved measurements, typically expressed as improved signal to noise ratio.

In an even further application, adjustment of the dimensions of the nanostructure may be suitable as a step in a measurement of a molecule. Variation in the dimension leads to variation of the plasmon structure leading to excitation. Hence, the variation and its impact on molecules or segments under measurement may end up in the electromagnetic radiation leaving the nanostructure, particularly in transmission and being optically detected.

According to a further aspect, a method for use with a device comprising a substrate, a patterned epitaxial layer on the substrate, a nanostructure penetrating the epitaxial layer, and an opening through the substrate underlying the nanostructure, wherein the epitaxial layer comprises a piezoelectric material and the method comprises the step of applying a predetermined voltage on the piezoelectrical material for deformation of the penetrating nanostructure.

According to again a further aspect, an apparatus comprises a membrane having a first and a second major surface and having a membrane penetrating nanostructure between the first and second major surfaces, the nanostructure comprising a nanopore with a varying diameter across the membrane and, in cross-sectional view, a substantially triangular shape. It further comprises a source of electromagnetic radiation that impinges radiation on the nanostructure in the direction of the first major surface, means for translocating molecules through the nanostructure, and a detection unit for detecting electromagnetic radiation that exits from the nanostructure away from the second major surface, transmission of electromagnetic radiation through the nanostructure being at least by excitation of surface plasmon polaritons in the nanostructure.

According to further aspect, a method for use with a membrane having a first and a second major surface and having a membrane penetrating nanostructure between the first and second major surfaces, the nanostructure comprising a nanopore with a varying diameter across the membrane and, in cross-sectional view, a substantially triangular shape. The method comprises a) directing electromagnetic radiation onto the nanostructure in the direction of the first major surface, b) translocating molecules through the nanostructure, and c) detecting electromagnetic radiation that exists from the nanostructure away from the second major surface, transmission of electromagnetic radiation through the nanostructure being at least by excitation of surface plasmon polaritons in the nanostructure.

BRIEF DESCRIPTION OF THE FIGURES

FIG. 5a-b shows in diagrammatical plan view further embodiments of the patterned epitaxial layer;

FIG. 6 shows in diagrammatical plan view a further embodiment of the patterned epitaxial layer;

DETAILED DESCRIPTION OF CERTAIN ILLUSTRATIVE EMBODIMENTS

Figure 1A:
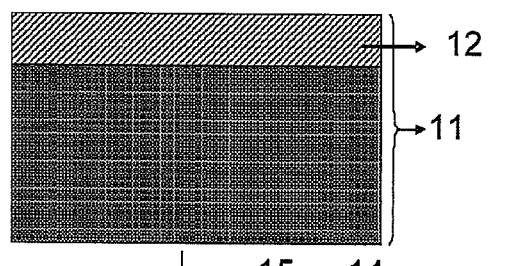
FIG. 1a-d shows in a series of diagrammatical cross-sectional views a first embodiment of the method according to one embodiment.

The present invention will be described with respect to particular embodiments and with reference to certain drawings but the invention is not limited thereto. The drawings described are only schematic and are non-limiting. In the drawings, the size of some of the elements may be exaggerated and not drawn on scale for illustrative purposes. The dimensions and the relative dimensions do not correspond to actual reductions to practice of the invention. Equal reference numerals in different figures refer to equal or like portions.

Furthermore, the terms first, second, third and the like in the description, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, bottom, over, under and the like in the description are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Certain embodiments relate according to one of its aspect to an optical sensing method for molecules. In its essence, the method comprises the steps of getting molecules to flow through a nanostructure, and characterizing the molecules individually. The nanostructure herein is more particularly a nanoscale passageway through which a molecule to be analyzed can pass through the passageway. More specifically, the characterization occurs while individual molecules flow through the nanostructure. In an advantageous embodiment, this characterization is carried out optically. One advantageous manner of carrying out the characterization optically involves the detection of radiation transmitted through the nanostructure while one molecules is present within the nanostructure.

Such transmission may be achieved through excitation of surface plasmon polaritons in particular. Additionally, there may be transmission of light through the penetrating nanostructure and re-emission. Surface plasmons relates to free space e.m. radiation impinging on the nanostructure. This radiation is converted to surface plasmon polaritons in the nanostructure. Dipolar excitation in the nanostructure decays radiatively, resulting in enhanced transmission. So the transmission of e.m. radiation (or enhanced transmission) through the nanostructure is at least by excitation of surface plasmon polaritons in the nanostructure.

In one embodiment, the nanostructure is defined in a device comprising a substrate and a patterned epitaxial layer on the substrate. The nanostructure penetrates herein the epitaxial layer. An opening extends through the substrate underlying the nanostructure. Tilted sidewalls of portions of the epitaxial layer face and limit a width of the penetrating nanostructure.

It has been observed that the use of a nanostructure with tilted sidewalls penetrating through an epitaxial layer results in an enhanced signal-to-noise ratio of the detected optical signal. The tilted sidewalls of the nanostructure may be defined by crystal facets of the epitaxial layer, particularly when growing the epitaxial layer using epitaxial lateral overgrowth. These crystal facets are substantially perfect and thus define dimensions of the nanostructure accurately. Specifically, epitaxial layers that can be grown on typical substrate materials such as silicon and sapphire have a crystal lattice, may be obtained with crystal facets suitably oriented so as to serve as the tilted sidewalls. Suitable materials are for instance III-V semiconductor materials. Due to the substantially perfect shape of the tilted sidewalls, noise in the detected optical signal is reduced. The crystal facets may further be covered with one or more layers. Such layers may include dielectric layers, adhesion layers, conductive layers, layers comprising nanoparticles or the like as preferred to optimize certain forms of molecular spectroscopy such as Raman spectroscopy.

Additionally, the tilted orientation is highly suitable so as to obtain a passageway for a limited number of molecules to be analyzed simultaneously. Preferably, the nanostructure is designed such that the number of molecules to be analyzed simultaneously passing the nanostructure is ten or less, more preferably five or less, and most preferably only one or two. Moreover, the shape with tilted side walls makes that the passageway with smallest diameter is located within a restricted volume. This restricted volume is clearly more restricted than if a pore with a single diameter were used. This adds again to improvement of signal-to-noise ratio of a detected signal.

The patterned epitaxial layer is an example of a membrane having a first and a second major surface. The nanostructure with tilted sidewalls may be or comprise a nanopore with a varying diameter across the membrane, and, in cross-sectional view, a substantially triangular shape. One therefore may suitably express the method in the embodiment of detection of transmitted radiation as a method comprising a) directing electromagnetic radiation onto the nanostructure in the direction of the first major surface, b) translocating molecules through the nanostructure, and c) detecting electromagnetic radiation that exists from the nanostructure away from the second major surface, transmission of electromagnetic radiation through the nanostructure being at least by excitation of surface plasmon polaritons in the nanostructure.

In an embodiment, a method as recited in any of the previous embodiments is disclosed wherein the nanostructure is configured to limit the passage of a sample material through the nanostructure to a single molecule at a time.

In an embodiment, a method as recited in any of the previous embodiments is disclosed wherein the single molecule may be a double stranded nucleic acid molecule. In another embodiment, the single molecule may be a single stranded nucleic acid molecule. In another embodiment, the single molecule may be a polypeptide molecule. In another embodiment, the single molecule may be a single ribosome. In another embodiment, the single molecule may be a cell. In another embodiment, the single molecule may be a viral particle.

In a further embodiment, the detection of the radiation occurs by molecular spectroscopy, and more specifically by Raman spectroscopy, molecular fluorescence spectroscopy or surface enhance infrared absorption spectroscopy. Certain embodiments of the invention can involve the use of nanoparticles to enhance the Raman signal obtained from nucleotides. The nanoparticles may be silver or gold nanoparticles, although any nanoparticles capable of providing a surface enhanced Raman spectroscopy (SERS), surface enhanced resonance Raman spectroscopy (SERRS) and/or coherent anti-Stokes Raman spectroscopy (CARS) signal may be used, e.g. Ag, Au, Cu, Al, Ni, Pt, Pd, particularly noble metals. A useful reference for particles and labels is: K. Kneipp, M. Moskovits, H. Kneipp (Eds.): Surface-Enhanced Raman Scattering—Physics and Applications, Topics Appl. Phys. 103, 1-18 (2006), which is incorporated herein by reference in its entirety. Nanoparticles of between 1 nm and 2 nm in diameter may be used. Nanoparticles with an average diameter of 10 to 50 nm, 50 to 100 nm or about 100 nm are contemplated for certain applications. The nanoparticles may be approximately spherical in shape, although nanoparticles of any shape or of irregular shape may be used.

Antenna structures can be added on the radiation entry side of the device to increase the portion of incident radiation that is collected and to achieve stronger field intensity in the penetrating nanostructure. On the radiation exit side an antenna can be used to increase the portion of radiation that is converted into free-space propagating radiation and/or to shape the exit beam.

Plasmonic nano-antennas can influence the behavior of optically active molecules in several ways. Firstly, due to the focusing of electromagnetic radiation to nanovolumes, molecules can be excited more efficiently. Secondly, the plasmon resonance perturbs the local electromagnetic mode density, modifying the decay rate of local dipole emitters. Such nanoantennas are particularly suitable in case that Raman spectroscopy, molecular fluorescence or surface enhanced infrared absorption spectroscopy is used.

In the case, e.g., of Raman spectroscopy, this double effect leads to the well known E4 dependence of the Raman scattering intensity on the local electric field. It further enables probing of vibrational transitions using optical excitation. Additional enhancement can be achieved using resonance Raman (illuminating in resonance with an electronic transition of the target molecule) or coherent anti-stokes Raman scattering (CARS) (a non-linear, 4-wave mixing process). Raman spectroscopy is particularly suitable for sensing segments of larger molecules, such DNA molecules.

In the embodiment of molecular fluorescence, there is a fundamental trade-off between field amplification by field confinement into the nanostructure and radiation that can leave the nanostructure, which is absent in the case of Raman. The shape of the pore is particularly relevant for the resolution, in order to limit the number of molecules contributing to the fluorescence. Nanoantennas located at the exit side lead again to a more effective outcoupling of radiation resulting from the fluorescence.

In the embodiment of surface enhanced infrared absorption spectroscopy, infrared radiation is directly coupled into the nanostructure. Thereto, the antenna is provided with structures having a mutual pitch which is larger than the pitch in case of fluorescence or Raman. This radiation is again converted by excitation into radiation transmitted through the nanostructure.

Figure 9:
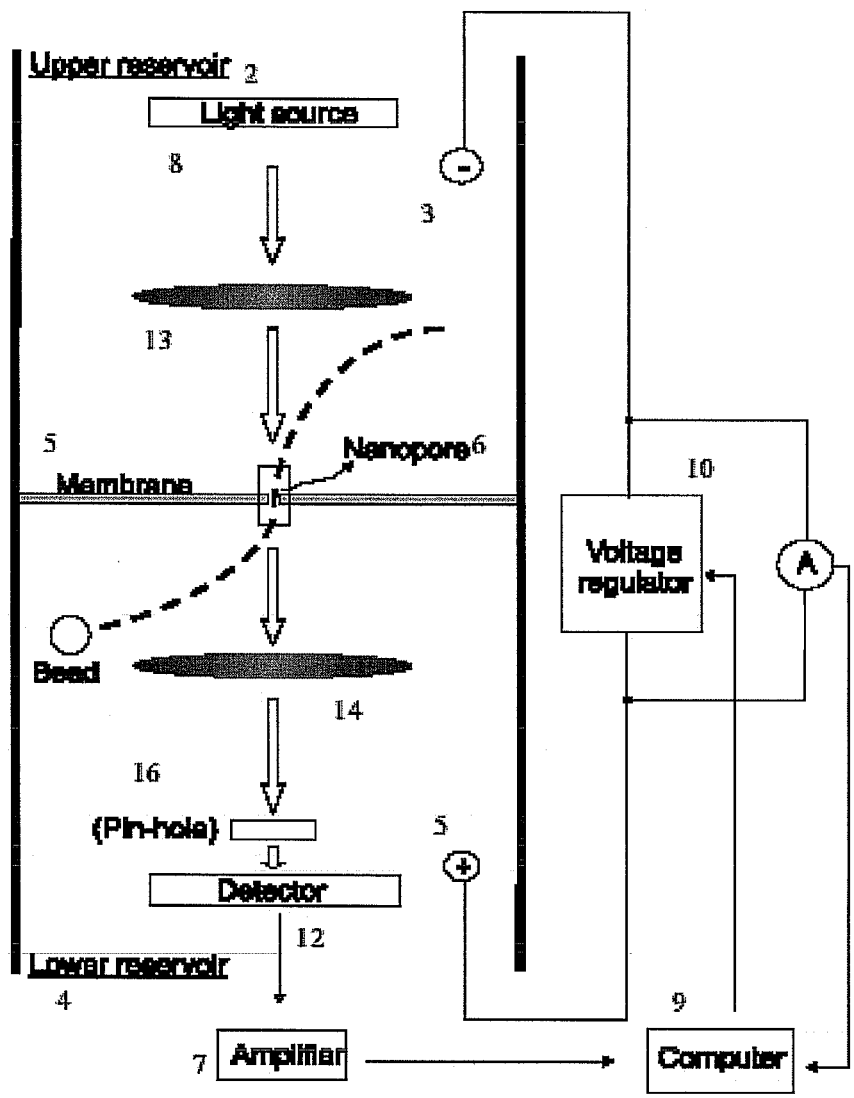
FIG. 9 shows a diagrammatical set up of an apparatus of one embodiment for use for optical detection of molecules.

FIG. 9 presents a sketch of an apparatus in accordance with an embodiment of the present invention. (The illustration is non-limiting and not to scale, some components in the drawing are not always required.) Two chambers 2,4 serve as fluidic reservoirs and are separated by a membrane 5 in which a membrane penetrating nanostructure such as a nanopore 6 is fabricated. A linear molecule such as comprising nucleic acids, DNA, RNA, single-stranded, double-stranded or triple stranded and any chemical modifications thereof a strand of DNA is translocated through the solid-state nanopore 6 by means of any suitable driving force, e.g. by electrophoresis. To this end, at least one electrode 3, 5 is mounted in each reservoir 2, 4, respectively and a voltage is supplied with a voltage regulator 10 (preferably feedback coupled). The apparatus further comprises a source of electromagnetic radiation such as a light source 8 (which can be, for example, a LED, a laser incandescent lamp or any other type of light source) and optionally a lens system 13. The light source may be placed inside the upper reservoir or may be external to the upper reservoir and may illuminate the nanopore 6 through a window. In some instances (for example CARS spectroscopy) more than one light source is used. The light is supplied from the top, i.e. from the upper reservoir 2 towards the lower reservoir 4. In the apparatus of FIG. 1 orthogonal light excitation is assumed but other angles of incidence at the nanopore 6 can also be chosen. The light interacts with the molecule inside the nanopore 6, this interaction is the basis for biomolecular analysis. Hence the nanopore can be an optical confinement. In one embodiment, important is the fact that electromagnetic radiation such as light that has been transmitted through the nanopore 6 (rather than only reflected light) is used for the measurements. In the lower reservoir an optical detector 12 and a light capture system such as a lens system 14 are mounted that collect the transmitted light. The detector 12 may be located outside the lower reservoir and may view the nanopore 6 through a window in the lower reservoir. The output of the detector 12 may be supplied to an amplifier 7 such as a preamplifier and the out put of the amplifier may be connected to read-out electronics. The read-out electronics may include a computing unit 9.

A membrane penetrating nanostructure should be understood as a structure having a nanoscale passageway through which a molecule can flow. The nanostructure is preferably designed such that the degrees of freedom for the movement of the molecule in the nanostructure is limited to a predefined direction, preferably from one side of the membrane to the other side of the membrane. Preferably, the movement should be limited to a 1D movement or line movement. The pore can be round, spherical, rectangular or can have any shape and can have a varying diameter across the thickness of the membrane. The pore is not limited to the region through which the molecule flows, but can be larger such that light can be coupled in the nanostructure. Therefore, the membrane penetrating nanostructure can be a nanopore, a nanoslit or a nanochannel.

Other than as fluidic channel and passage for molecules, the membrane penetrating nanostructure such as the nanopore 6 acts as a channel for light transmission. In order to achieve light transmission through the sub-wavelength hole, the properties of surface plasmons polaritons are used. The transition of e.m. radiation through the penetrating nanostructure is a combination of up to three effects: surface plasmons, transmission of light and re-emission. Surface plasmons relates to free space e.m. radiation (the impinging radiation) being converted to surface plasmon polaritons in the coupled pore/cavity system. The dipolar excitation in the pore decays radiatively, resulting in enhanced transmission. So the transmission of e.m. radiation (or enhanced transmission) through the nanostructure is at least by excitation of surface plasmon polaritons in the nanostructure.

Furthermore, by nanostructuring the membrane on top to maximize the capture process and nanostructuring the backside to maximize the re-emission process, the transmission can be improved further and/or maximized. Transmission of light through this optical channel can occur based on two principles: via waveguiding of propagating modes in the channel or via evanescent non-propagating modes that couple through the channel to modes on the exit side.

Preferably, the nanostructure with tilted sidewalls is created such as to create an electromagnetic hotspot. The hotspot is the location where the optical interaction is strongest and where structural or chemical information is harvested. It provides a smaller sensing region than what can be achieved with traditional lens structures or photonic components. The field confining structure provides plasmonic field confinement leading to localization based on gap mode resonance, at the hotspot. As a result, the electromagnetic field gets concentrated in the hotspot. Therewith, the hotspot effectively amplifies the optical signal. The electromagnetic field results from the interaction of the electromagnetic radiation with the matter present. Means for enhancement of the field strength, and thus means for creation of the hotspot, include plasmon carrying metal structures, in particular nano-antennas, and a nanostructure in which cavity effects occur, particularly with a varying diameter. In the latter case, the nanostructure is preferably designed such that the hotspot is present at the position at which the—inner—diameter is smallest. However, alternative shapes of the nanostructure leading to resonance in a limited volume thereof are not excluded.

Antenna structures can be added on the light entry side to increase the portion of incident light that is collected and to achieve stronger field intensity in the nanopore 6. On the light exit side an antenna can be used to increase the portion of light that is converted into free-space propagating light and/or to shape the exit beam. The radiation pattern of the light exiting the membrane can be controlled through design: a dipolar radiation pattern, for example, can be achieved, or, in a more sophisticated implementation, antenna structures on the exit side can be provided to guide the light. This feature can be important for improving signal-to-noise and further reduction of background signals: the optical collection system in the lower reservoir can be optimized for collecting light emanating from the nano-aperture, a directed output signal can be detected with greater efficiency and leads to a better signal-to-noise. Furthermore, unwanted light collection is further suppressed. In the example of FIG. 1, this can be achieved with a lens 14 and a pinhole 16 placed in a conjugate plane. Examples of antenna structures are gratings and series of metal stripes. The metal stripes are suitably oriented in parallel to a slit serving as an entry of the nanostructure. However, the metal stripes could alternatively be oriented in a radial pattern around a centre defined by the nanostructure.

In a further embodiment, antennas can be employed to confine low-energy electromagnetic radiation, using their non-linear properties. For increasing degrees of field confinement, nonlinear effects become more important. These effects include wave mixing, meaning that locally electromagnetic waves with designed energies can be excited. Wave mixing includes second harmonic generation, sum frequency generation, difference frequency generation (all of these are 3-wave mixing) and four-wave mixing. Using e.g. difference frequency generation, locally low-energy electromagnetic waves can be excited. Gutjahr-Loser et al employed the non-linear properties of a scanning-electron-tunneling microscope to convert high-energy electromagnetic radiation (THz) to low-energy radiation (GHz), and succeeded in exciting local ferrimagnetic resonances in a ferrimagnetic material using THz light irradiation. Similarly, using plasmonic nano-antennas, in accordance with an aspect of the present invention magnetic resonances can be excited on a local (nano) scale. This allows local excitation of ferromagnetic resonance (FMR), electron spin resonance (ESR), and nuclear magnetic resonance (NMR). Due to its chemical selectivity, especially NMR is particularly attractive. Usually NMR is being used on macro-scale samples due to the difficulty to localize magnetic fields.

According to another aspect of the invention, a device is provided comprising a substrate, a layer present thereon and a nanostructure penetrating the layer, which nanostructure defines a nanoscale passageway through which a molecule to be analyzed can pass through the passageway, wherein the nanostructure has, in cross-sectional view, a substantially triangular shape.

The inventors have combined advanced know-how from the domains of optical analysis, biomolecules and semiconductor processing to end up at a device with surprising properties, i.e. that improved signal-to-noise ratio of the optical detection can be achieved by means of exploiting growth parameters of epitaxial layers grown on a substrate.

In an embodiment, the nanostructure is a 3 dimensional structure such as, but not limited hereto, a pore, a hole or a channel. The shape may be circular, triangular, quadratic, oval or a slit. The pore can be round, spherical, rectangular or can have any shape and has a varying diameter across the thickness of the membrane. The term nanostructure should be construed broadly to include nanoslits (two-dimensional equivalent) or nanochannels. In a particular embodiment, the dimensions which determines whether a molecule will pass, e.g. the distance across a slit, or the diameter of a hole, should be smaller than 1 μm, smaller than 100 nm, smaller than 50 nm and preferably smaller than 10 nm, e.g. less than 5 nm, less than 2 nm e.g. 1 nm.

Most suitably, the nanostructure with a substantially triangular shape in cross-sectional view is implemented with an epitaxial layer having preferential side faces defining tilted sidewalls of the nanostructure. Using an epitaxial layer provides nanostructures with accurate dimensions and a very small number of dislocations. Moreover, the nanostructure can be achieved in accordance with semiconductor technology. One embodiment thereof is wet etching. This is suitable for a silicon based material. Another embodiment is epitaxial lateral overgrowth. This is particularly suitable for III-V semiconductor materials, and more specifically for group-III nitride materials. The epitaxial lateral overgrowth results in crystal facets on the surface.

The substrate is particularly a substrate that allows epitaxial growth of a group III nitride device. The substrate may be Si, SiC, Sapphire, AlN, GaN, AlGaN, LiNbO3, ZnO, MgO or porous Si. The substrate may also be formed by combinations of the layers recited above. In an alternative embodiment, the substrate may be a substrate as mentioned in the previous embodiment covered with a group III nitride layer. In a preferred embodiment, the substrate is a silicon substrate covered with an AlGaN layer.

In a particular embodiment of the present invention, the epitaxial layer is a layer comprising a piezoelectric material (also called piezoelectric layer). The piezoelectric material is a material showing a piezoelectric effect. The piezoelectric material may be a group III nitride material. The piezoelectric material may also be selected form the group including berlinite ($AlPO_4$), cane sugar, quartz, Rochelle salt, topaz, tourmaline-group minerals, gallium orthophosphate ($GaPO_4$), Langasite ($La_3Ga_5SiO_{14}$), barium titanate ($BaTiO_3$), lead titanate ($PbTiO_3$), lead zirconate titanate ($Pb[Zr_xTi_{1-x}]O_3$ $0<x<1$)—more commonly known as PZT, potassium niobate ($KNbO_3$), lithium niobate ($LiNbO_3$), lithium tantalate ($LiTaO_3$), sodium tungstate ($Na_2WO_3$), $Ba_2NaNb_5O_5$, $Pb_2KNb_5O_{15}$, Polyvinylidene fluoride (PVDF), Sodium potassium niobate (KNN) and Bismuth ferrite ($BiFeO_3$).

Suitably, at least one electrode operatively associated with the piezoelectric layer is present. The electrode is for applying a voltage on the piezoelectrical layer. The electrode is for applying a voltage on the piezoelectric material thereby deforming the piezoelectric material and consequently the nanostructure penetrating the piezoelectric layer. The dimensions of the nanostructure can be adjusted. When a voltage is applied to the piezoelectric material, the piezoelectric material deforms. When a voltage is applied, an electrically induced mechanical stimulus is applied to the piezoelectric layer, which can deform resulting in a deformation of the membrane penetrating nanostructure. A deformation of the membrane penetrating nanostructure can be, but is not limited hereto, a change of the inner diameter of the membrane penetrating nanostructure. The change can be an increase or decrease of the inner diameter of at least a part of the membrane penetrating nanostructures. Thus, the device may have an adjustable membrane penetrating nanostructure. By applying a predetermined voltage on the piezoelectrical material, the inner diameter of the membrane penetrating nanostructure can set to a predetermined value.

In one embodiment, a first and a second electrode may be present on opposite sides of the piezoelectric layers. The field to be applied is then applied in a direction perpendicular to a plane through the piezoelectric layer. Specific electrode designs may be applied so as to stimulate deformation of the piezoelectric layer in a direction substantially parallel to the plane through the piezoelectric layer. An example hereof is known from WO-A 2005/064634. The piezoelectric layer is suitably split into independent portion located on opposite sides of a nanostructure. It is not necessary that the portions on both sides of the nanostructure are provided with electrodes so as to be deformed. I.e. if the piezoelectric layer comprises a first portion on a first side of the nanostructure and a second portion on a second side of the nanostructure opposite to the first side, then the at least one electrode may be present on the first side (suitably as a pair of electrodes between which the piezoelectric layer is sandwiched), while the second portion of the piezoelectric layer is not made deformable, i.e. there are no electrodes.

In a suitable implementation, the piezoelectrical layer is present on a buffer layer. The buffer layer is suitably made of a material structurally similar or identical to the piezoelectrical layer. A bottom electrode is suitably provided on top of the buffer layer In a further implementation, the piezoelectrical layer laterally overhangs a cavity at least partially. Sidewalls of the cavity may be defined by the buffer layer. This implementations enhance deformation of the piezoelectrical layer in the desired direction.

The feature of a piezoelectric layer acting to adjust the nanostructure may be beneficial also in combination with a nanostructure without varying diameter. Thus, according to another aspect of the invention, a device is provided comprising a substrate, a piezoelectrical layer present thereon, an electrode operatively associated with the piezoelectric layer. The device further comprises an adjustable nanostructure penetrating the piezoelectrical layer, the nanostructure having a nanoscale passageway through which a molecule to be analyzed can pass through the passageway and the nanostructure being adjustable by means of application of a voltage on the electrode for deformation of the piezoelectric layer.

The devices according to one embodiment are most suitably manufactured by growing an epitaxial layer on a substrate in a certain manner. Suitably, particularly from the processing perspective, the substrate is a semiconductor substrate. Good results have been obtained with epitaxial layers comprising a semiconductor material, in particularly a III-V material and more preferably a III-nitride type material. Most suitably, use is made of techniques known per se as epitaxial lateral overgrowth (ELO, ELOG). Hiramatsu describes the ELO technique in detail in J. Phys. Condens. Matter, 13 (2001), 6961-6975, which disclosure is herein incorporated by reference in its entirety. According to one embodiment, the ELO technique is skillfully used for obtaining better and improved devices that open up a new realm of characterizing molecules. In accordance with one embodiment, a nanostructure penetrating the epitaxial layer is formed. In another embodiment, the patterning layer can be formed by patterning the substrate, the patterned layer may be AlInGaN, AlInGaP, AlInGaNP, AlInGaAs, SiC, Si, SiGe, Ge, antimonides, (Mg) ZnO, or ZnSe(Te).

FIG. 1a-d shows in a diagrammatical cross-sectional view four stages in the manufacture of the device according to one embodiment. It is observed for clarity that the cross-sectional view of FIG. 1a-e does not show tilted sidewalls. As will be clear from the following, such tilted sidewalls may be obtained by controlling growth parameters and/or by adequate definition of the mask used in the patterned growth of the epitaxial layer.

FIG. 1a shows a first stage, in which a substrate 11 is provided. The substrate comprises a carrier layer and a buffer layer 12. The buffer layer is particularly a layer of a group-III-V material, more suitably, a group-III nitride material. An example of a material suitable for a buffer layer is AlGaN, wherein the relative content of Al and Ga may vary. It is deemed convenient to start with a layer of AlN and increase the Ga-content stepwise or gradually. The buffer layer is typically grown in an MOCVD-reactor on top of a nucleation layer. The carrier layer suitably comprises a semiconductor substrate. Several options of semiconductor substrate have been tried out for growth of group III-nitride materials. Typical materials currently in use include sapphire, silicon (001) and silicon (111), the latter particularly in the form of a silicon (111) top layer of a silicon-on-insulator substrate having a buried insulator layer and a handling wafer.

Figure 1B:
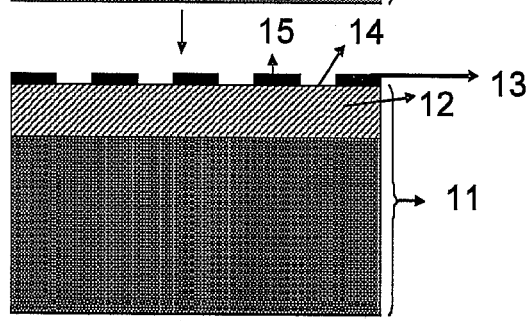

FIG. 1b shows a second stage in the manufacturing. Herein a patterned layer 13 is deposited on the buffer layer 12. The mask layer suitably comprises a dielectric layer, such as silicon nitride or silicon oxide, though other materials such as metals are not excluded. The patterned layer 13 is patterned so as to define openings 14 and masks 15. Specific designs of the patterned layer 13 will be discussed below.

Figure 1C:
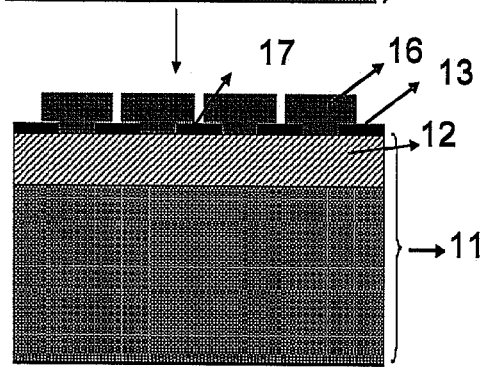

FIG. 1c shows a third stage in the manufacturing. Herein, an epitaxial layer 16 has been grown. The growth occurs vertically from the opening 14 and laterally over the mask 15, starting from the opening 14. The overgrowth step is selected such that the ratio of the lateral growth versus the vertical growth is in the range of 1/20 to 20. Due to the selectivity of a group-IIIV material, more in particular a group-III nitride layer over $SiO_2$ and $Si_xN_y$, GaN can only be grown through exposed window region. The group-IIIV layer is suitably chosen from the group of GaN, AlGaN, AlN, AlInGaN, AlInGaP, AlInGaNP, AlInGaAs and combinations hereof. The epitaxial layer may be provided as a number of layers with mutually different composition. The growth process is terminated before coalescence of layer portions occurs. This termination is based on end point detection. As a result, a nanostructure 17 is formed penetrating the epitaxial layer 16. The design of the nanostructure is dependent on various growth and design parameters, including growth temperature and pressure, width of the mask 15, orientation of the mask 15 relative to specific crystal lattice orientations of the material, and the material of the epitaxial layer. While not shown here, the growth is defined so as to obtain tilted side walls of the nanostructure 17, effectively side faces of the epitaxial layer portions 16. Though not shown, a protective top layer is suitably added on top of the epitaxial layer 16. Such a protective top layer is for instance a dielectric layer of silicon nitride. The protective top layer may be grown in situ, i.e. in the same CVD reactor subsequent to the growth of the epitaxial layer by changing composition of reactor gases and possibly temperature and pressure. On top of the epitaxial layer or the protective top layer a layer of conductive material may be deposited. Particularly suitable examples of conductive materials are noble metals, such as Pt and Au. However conductive materials such as TiN, TiWN, TiW, TaN, Ta, W, combinations and allows thereof may be beneficial. Such layers could further be used as adhesion layers between the epitaxial layer and/or protective top layer and the noble metal. Antenna structures may be defined in the conductive material, for instance by patterning the conductive material.

While providing the conductive material, the nanostructure 17 may be closed temporarily by deposition of a sacrificial layer. One type of advantageous sacrificial layer comprises a material that can be decomposed into gaseous components by heating. Further information hereon can be found in WO-A 2007/054867, which is incorporated herein by reference in its entirety. However, it is not deemed necessary to close the nanostructure temporarily. Instead, the sidewalls of the nanostructure 17 may be covered with the conductive material as well. Such coverage is suitably obtained by deposition of the conductive material from the vapor phase, e.g. by means of CVD, MOCVD, ALD or the like. Such coverage of the sidewalls of the nanostructure 17 is most suitably carried out after removal of the patterned layer 13.

Figure 1D:
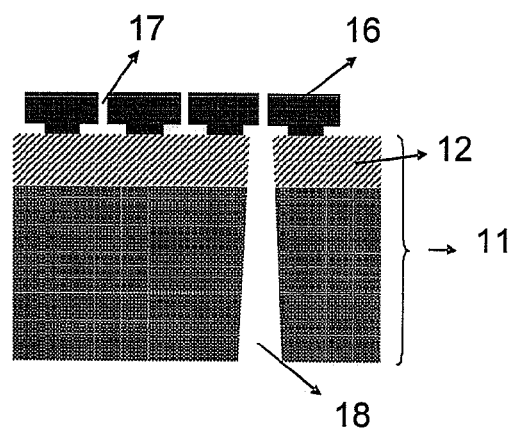

FIG. 1d shows a fourth stage in the manufacturing. Herein the patterned layer 13 has been removed and a through-hole 18 has been created through the substrate 11. Removal of the patterned layer 13 suitably is carried out with wet or dry etching. It is deemed most beneficial to remove the patterned layer 13 completely, though it is not excluded that an aperture is made in the patterned layer at a location corresponding to that of the nanostructure 17. The through-hole 18 is suitably made by wet-etching from a rear side of the substrate 11. The processing from the rear side typically is a one of the last step in the processing. It may be preceded by the provision of a cover and/or temporary carrier on top of the epitaxial layer 16. Such a cover may simultaneously act as an enclosure of a chamber in which fluid is to be provided, the fluid comprising molecules to be analyzed. An optically transparent cover is preferred so that electromagnetic radiation directed to the nanostructure may pass through the cover.

As is clear from the FIG. 1a-d, the non-coalesced layer thus forms nano-slits, which can be used as channels for microfludics in the lateral configuration. In addition, the nano-slits or nanopores can be integrated in a vertical structure if the substrate is removed in the region under the nanopore or nanoslit (see 18). There are a few possible ways to remove the substrate (see FIG. 1b). For example, in the case of sapphire substrates, laser liftoff may be used. When silicon substrates are used, a simple wet chemical etching in KOH, dry etching or grinding etc all is possible to remove silicon.

In selective area growth, the growth direction can be either vertical or lateral. By enhancing lateral growth, the size of nano-structures can be adjusted beyond the lithography limit. Furthermore, during lateral growth, perfect facets can be observed. A few referred facets for example {11-20}, {11-22} and {1-101} have been reported in lateral GaN growth, which depends on the growth parameters including growth temperature, V/III ratio and growth pressure. The growth temperature can be in the range of 500 to 1200° C. The growth pressure is be tuned from 10 to 1000 Torr. The V/III ratio is the ratio of the total group V flux to group III, which can be from 100 to 10000. These facets will form excellent nanostructures. Examples of nanostructures are nano-pores and nano-slits. The cross section of the nano structures can also be controlled by the growth parameters.

Figure 2A:
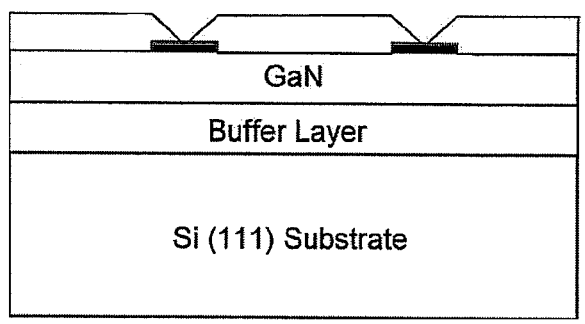
FIG. 2a-b show in diagrammatical, cross-sectional view a second embodiment of the method according to one embodiment.
Figure 2B:
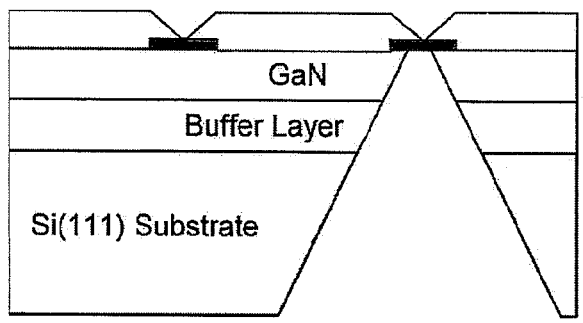

FIG. 2a-b shows in cross-sectional view two stages in the manufacturing. FIG. 2a thereof shows a substrate structure comprising a Si (111) substrate, a buffer layer and a first GaN layer. The patterned layer 13 is provided thereon, and is overgrown with the epitaxial layer 16. As shown herein, the epitaxial layer 16 is divided into portions, each with tilted side faces including an oblique angle to the substrate plane.

FIG. 2b shows the device after etching through the substrate from its rear side. The patterned layer 13 is herein used as etch stop layer. It can be removed subsequently.

In an embodiment, the patterned layer has a pattern of openings exposing portions of the surface. The pattern of openings is designed such that the nanostructures are formed on a predetermined location. The dimensions of the opening in the patterning layer are between 10 nm and 100 µm, between 10 nm and 10 µm. between 10 nm and 1 µm. The epitaxial layer is suitably formed in a thickness between 5 nm and 5 µm, between 5 nm and 2 µm or between 5 nm or 1 µm. In order to have tilted sidewalls that are suitable for reducing the dimension to a minimum size and for adequately guiding light, it is deemed suitably that the thickness is in the micrometer range.

Figure 3:
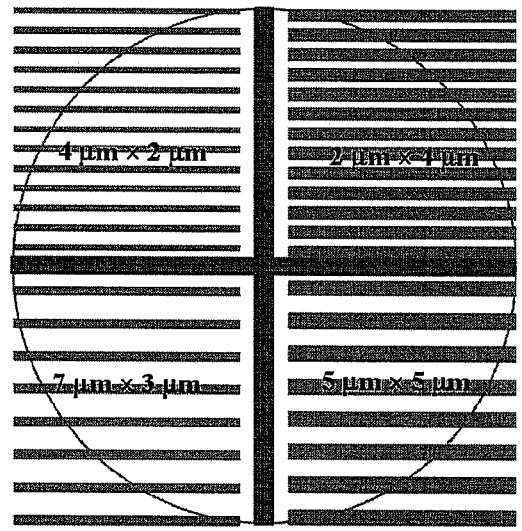
FIG. 3 shows a design of a mask used in the method according to one embodiment.

FIG. 3 shows a design of a mask used in first experiments. The mask has been prepared with various widths of windows and mask materials. The mask is a stripe mask, i.e. the pattern comprises several stripes in parallel to each other. FIG. 3 (a) shows a mask wherein the width of the mask layer is 2 µm and the width of the openings is 4 µm. FIG. 3 (b) shows a mask wherein the width of the mask layer is 4 µm and the width of the openings is 2 µm. FIG. 3 (c) shows a mask wherein the width of the mask layer is 3 µm and the width of the openings is 7 µm. FIG. 3 (d) shows a mask wherein the width of the mask layer is 5 µm and the width of the openings is 5 µm. The pattern is formed by using a normal optical lithography with a resolution of 1 µm. After lithography, the sample was reloaded into the MOCVD reactor to grow a certain thickness GaN. Because of the difference in the mask width, the lateral growth region shows different morphology. In the quarter with 2 µm mask width, the layer is fully coalesced. In the quarters with 3 µm mask width, 4 µm mask width and 5 µm mask width, some nano-slits are formed. It is observed for clarity that one may also obtain nanoslits with a mask having a width of 2 µm by defining different growth conditions and/or terminating the growth earlier. This however was not done within the context of the first experiments.

In order to obtain crystal facets, one may align the extension of the mask to a suitable crystal orientation. When a silicon (111) substrate is used, the stripe mask can be align to be parallel to the <11-2> direction. The formed facets are {11-20} or {11-22}. The stripe can also be aligned to <1-10> direction and then the preferred facets are {1-101}. The angle with the substrate plane is different for each of the 111-201, {11-22} and {1-101} facets.

The sample was grown at a temperature above 1000° C.; the growth pressure is 100 Torr and the V/III ratio is about 2000. The growth rate in the vertical direction is about 40 nm/min. The lateral growth rate can be varied in the range of 2 to 200 nm/min, which depends on the orientation of the facets. The growth time is adjusted from 1000 s to 2000 s. By fine tuning the growth parameters including growth time, growth rate and growth temperature, a nano-slit is formed with a width of <40 nm. This width is even better than the one achieved in e-beam lithography.

In addition to the definition of the mask, the shape of the sidewall may be controlled with growth parameters i.e. growth temperature and growth pressure. It was found in systematic experiments on epitaxial lateral overgrowth of GaN, that four different regions exist. In region I, with a growth temperature below 925° C., morphologies are poor. There are large pits on the top and inclined {1-101} surfaces. Region II is defined as a region with a growth temperature from 925° C. up to 950° C. at a pressure of 40 Torr, and up to a 1000° C. at a pressure of 500 Torr. In this region II, the side walls are composed of the {11-22} surfaces like in region I, while the {0001} surface becomes smooth. Region III is defined as a region with a growth temperature from 950° C. to 1010° C. at a pressure of 40 Torr, and from 1000° C. to 1060° C. at 500 Torr. In this region, the side walls are varied from the inclined {11-22} surfaces to the vertical {11-20} surfaces. In region IV, which is located above region III, the {0001} surface becomes rough. Clearly, the exact growth conditions further depend on mask orientation as well as material of the epitaxial layer.

Figure 7A:
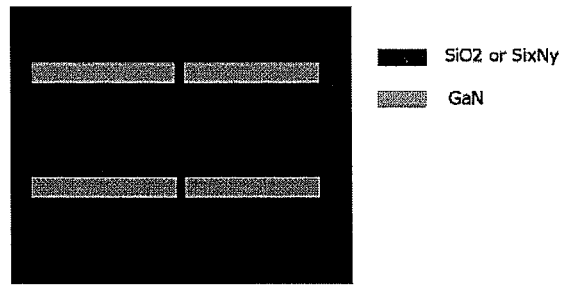
FIG. 7a-b shows in diagrammatical plan view a mask and a patterned epitaxial layer formed with growth on the mask.
Figure 7B:
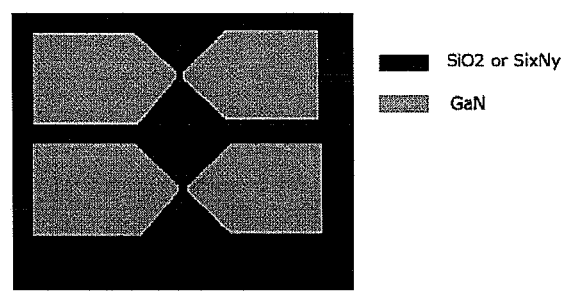

FIGS. 7a and b are diagrammatical plan views of a mask and a resulting epitaxial layer having crystal facets. In FIG. 7a, the GaN refers to the underlying substrate, e.g. the buffer layer 12, while the SiO$_2$ or SixNy refers to the mask, e.g. the patterned layer 13. In FIG. 7b, the GaN refers to the epitaxial layer 16, and the SiO$_2$ or SixNy still refers to the patterned layer 13.

FIG. 7a shows a mask 13 that largely covers the substrate, except for slit-shaped openings. Shown are two rows of slits parallel to each other, each row of slits comprising a first and a second slit mutually separated by a wall-shaped portion of the mask 13. The nanostructure 17 is actually to be formed on this wall-shaped portion. Its dimensions are thus a relevant parameter for defining the nanostructure.

FIG. 7b shows the resulting epitaxial layer 16. As is clear from this top view, at least two crystal facets are formed. The shapes define a nanostructure in the form of a slit and adjacent thereto restricted volumes. The portions of the epitaxial layer in the first and the second row are mutually separated over a distance. This distance may be exploited as an access channel. Its shape may be further optimized by tuning the design of the mask shown in FIG. 7a.

Figure 8:
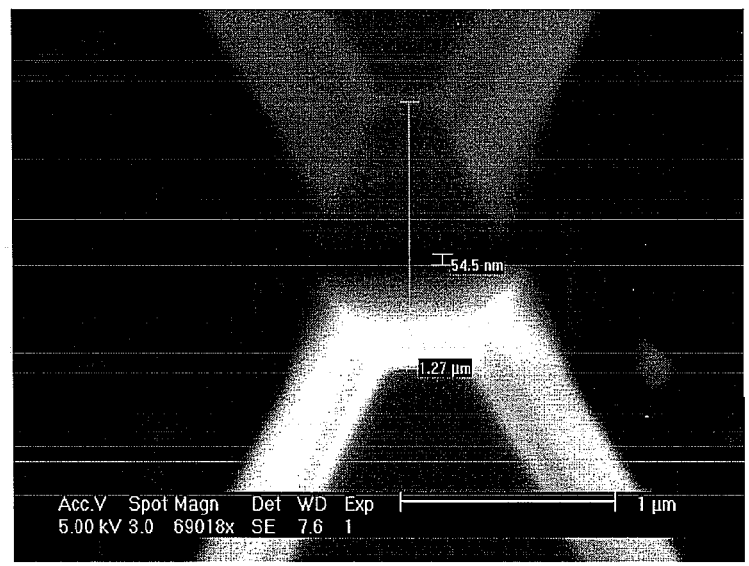
FIG. 8 shows a top view, obtained with SEM imaging, of the epitaxial layer in one embodiment of the device according to one embodiment.

FIG. 8 is a top view of a part of the epitaxial layer in an image made by scanning electron microscopy (SEM). The top view also shows the nanostructure between a first and second portion of the epitaxial layer. The image effectively corresponds to a part of FIG. 7b. It is clear from this figure, that the nanostructure 17 is provided with tilted sidewalls defined by the crystal facets. In this manner, the width of the nanostructure varies from 54 nm up to 1.27 microns. The epitaxial layer 16 herein has crystal facets with different orientation. In this manner, restricted volumes are created adjacent to the slit-shaped nanostructure. These restricted volumes are highly suitable for provision of fluid to the nanostructure without giving rise to turbulence and the like.

Figure 10:
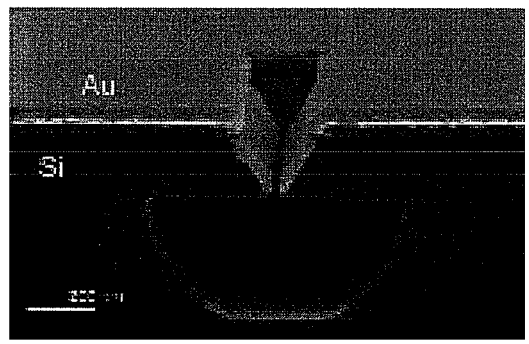
FIG. 10 shows a bird's eye view, obtained with SEM imaging, of the device in another embodiment.

FIG. 10 is a bird's eye view of a part of the epitaxial layer in an image made by scanning electron microscopy (SEM). The device shown here comprises an epitaxial layer of silicon. The device comprises a nanostructure with a triangular shape in cross-sectional view. The side faces of the epitaxial layer are herein tilted side walls of the nanostructure. This nanostructure is created by wet etching of the epitaxial layer. It is further shown in this Figure that the nanostructure is covered with a gold (Au) layer.

Figure 4:
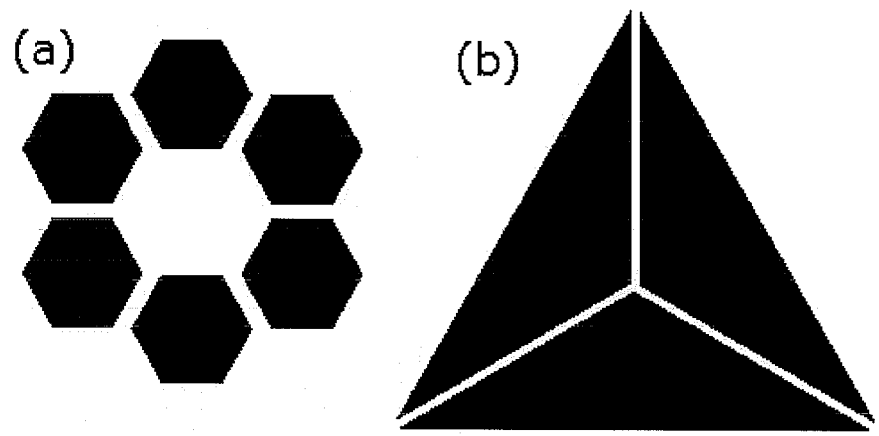
FIG. 4a-b show in diagrammatical plan view several embodiment of the patterned epitaxial layer.

FIGS. 4, 5 and 6 show diagrammatical plan views of further embodiments of the patterned epitaxial layer. The grey area herein defines the epitaxial layer, whereas the open area defines the nanostructure. The design of FIG. 4a effectively provides six nanostructures. Light may be focused on each of these slits individually, such that one may carry out six measurements simultaneously. It is herein clear that the number of detection sites may in this manner be expanded further. The design of FIG. 5b is a ring-shaped nanostructure. Such a ring shape, and particularly one shown here with a high degree of internal symmetry, is effective as a plasmonic resonator. In other words, this structure enhances the resonance of surface plasmons within the nanostructure. It is therefore expected to result in a further enhanced signal-to-noise ratio. The design of FIG. 6 shows a combination of an access channel and a nanostructure. The design moreover includes nanostructures with different widths. Clearly, the nanostructure with the smallest width is deemed most beneficial for the sensing of individual molecules or segments thereof.

The foregoing description details certain embodiments of the invention. It will be appreciated, however, that no matter how detailed the foregoing appears in text, the invention may be practiced in many ways. It should be noted that the use of particular terminology when describing certain features or aspects of the invention should not be taken to imply that the terminology is being re-defined herein to be restricted to including any specific characteristics of the features or aspects of the invention with which that terminology is associated.

While the above detailed description has shown, described, and pointed out novel features of the invention as applied to various embodiments, it will be understood that various omissions, substitutions, and changes in the form and details of the device or process illustrated may be made by those skilled in the technology without departing from the spirit of the invention. The scope of the invention is indicated by the appended claims rather than by the foregoing description. All changes which come within the meaning and range of equivalency of the claims are to be embraced within their scope.

What is claimed is:
1. A device comprising:
   a substrate;
   a layer present on the substrate;
   a nanostructure penetrating the layer and defining a nanoscale passageway through which a molecule to be ana- lyzed passes, wherein the nanostructure has, in cross-sectional view, a substantially triangular shape;
a source of electromagnetic radiation configured to impinge radiation on the nanostructure from a first side;
means for translocating molecules through the nanostructure; and
a detection unit configured to detect electromagnetic radiation that exits from the nanostructure away from a second side opposite to the first side, wherein transmission of electromagnetic radiation through the nanostructure is at least by excitation of surface plasmon polaritons in the nanostructure;
wherein the substrate comprises a through-hole in alignment with the nanostructure; and
wherein the layer is an epitaxial layer provided with crystal facets facing the nanostructure.

2. The device as claimed in claim 1, wherein a first and a second crystal facet are present on opposite sides of the nanostructure, thus defining a nanostructure with tilted walls.

3. The device as claimed in claim 2, wherein further crystal facets are present adjacent to the first and second facet, wherein a couple of the further crystal facets adjacent to the first and second facet defines a restricted volume adjacent to the nanostructure.

4. The device as claimed in claim 3, wherein the nanostructure is laterally present within a first and a second restricted volume, the volumes having a shape symmetrical around the nanostructure.

5. The device as claimed in claim 1, further comprising an access channel present between a first and a second crystal portion of the epitaxial layer, the access channel extending to the nanostructure.

6. The device as claimed in claim 1, wherein the nanostructure extends around a first crystal portion of the epitaxial layer, thus providing a ring-shaped nanostructure acting as a plasmonic resonator.

7. The device as claimed in claim 1, wherein a field confining structure is defined by the shape that creates an electromagnetic hotspot within the nanostructure.

8. The device as claimed in claim 1, further comprising at least one nano-antenna on a first side and/or an opposed second side of the device, the sides being parallel to a plane through the substrate, the nanoantenna serving to guide surface plasmon waves to the nanostructure and/or transmit light emitted from the nanostructure to a detector.

9. The device as claimed in claim 1, wherein the penetrating nanostructure is an adjustable penetrating nanostructure.

10. The device as claimed in claim 9, wherein the epitaxial layer is a layer comprising a piezoelectric material and the device comprises at least one electrode operatively associated with the piezoelectric layer for deformation of the piezoelectric layer and therewith deformation of the nanostructure.

11. A device comprising:
a substrate;
a piezoelectrical layer present on the substrate;
an electrode operatively associated with the piezoelectric layer; an adjustable nanostructure penetrating the piezoelectrical layer, the nanostructure having a nanoscale passageway through which a molecule to be analyzed passes, the nanostructure being adjustable by a voltage applied on the electrode for deformation of the piezoelectric layer;
a source of electromagnetic radiation configured to impinge radiation on the nanostructure from a first side;
means for translocating molecules through the nanostructure; and
a detection unit configured to detect electromagnetic radiation that exits from the nanostructure away from a second side opposite to the first side, wherein transmission of electromagnetic radiation through the nanostructure is at least by excitation of surface plasmon polaritons in the nanostructure;
wherein the substrate comprises a through-hole in alignment with the nanostructure; and
wherein the piezoelectric layer is an epitaxial layer provided with crystal facets facing the nanostructure.

12. A method of analyzing molecules with a device, the device comprising a substrate, a patterned epitaxial layer on the substrate, a nanostructure penetrating the epitaxial layer, and an opening through the substrate underlying the nanostructure, wherein tilted sidewalls of portions of the epitaxial layer face and limit a width of the penetrating nanostructure, the method comprising:
getting molecules to flow through the nanostructure, and characterizing the molecules;
wherein light is coupled into the nanostructure from a first side, and the molecules are characterized optically using excitation of surface plasmon wave in the nanostructure.

13. The method as claimed in claim 12, wherein the characterization is based on electromagnetic radiation transmitted through the nanostructure to a second side at least by the excitation of surface plasmon wave in the nanostructure.

14. The method as claimed in claim 12, wherein the nanostructure is configured to limit passage of a sample material through the nanostructure to a single molecule at a time.

15. The method as claimed in claim 12, wherein the epitaxial layer comprises a piezoelectric material and a predetermined voltage is applied on the piezoelectrical material to adjust an inner diameter of the penetrating nanostructure to a predetermined value.

16. A method for use with a device, the device comprising a substrate, a patterned epitaxial layer on the substrate, a nanostructure penetrating the epitaxial layer, and an opening through the substrate underlying the nanostructure, wherein the epitaxial layer comprises a piezoelectric material, the method comprising:
applying a predetermined voltage on the piezoelectrical material for deformation of the penetrating nanostructure;
wherein light is coupled into the nanostructure from a first side, and the molecules are characterized optically using excitation of surface plasmon wave in the nanostructure.

17. The method as claimed in claim 16, wherein the deformation adjusts an inner diameter of the penetrating nanostructure to a predetermined value.

18. An apparatus comprising:
an epitaxial layer having a first and a second major surface and a layer penetrating nanostructure between the first and second major surfaces, the nanostructure comprising a nanopore with a varying diameter across the eptaxial layer and, in cross-sectional view, a substantially triangular shape;
a source of electromagnetic radiation that impinges radiation on the nanostructure in the direction of the first major surface;
a translocating unit configured to translocate molecules through the nanostructure; and
a detection unit configured to detect electromagnetic radiation that exits from the nanostructure away from the second major surface, transmission of electromagnetic radiation through the nanostructure being at least by excitation of surface plasmon polaritons in the nanostructure.

19. A method of analyzing molecules with an epitaxial layer, the epitaxial layer having a first and a second major surface and having a membrane penetrating nanostructure between the first and second major surfaces, the nanostructure comprising a nanopore with a varying diameter across the epitaxial layer and, in cross-sectional view, a substantially triangular shape, the method comprising:
    directing electromagnetic radiation onto the nanostructure in the direction of the first major surface;
    translocating molecules through the nanostructure; and
    detecting electromagnetic radiation that exists from the nanostructure away from the second major surface, transmission of electromagnetic radiation through the nanostructure being at least by excitation of surface plasmon polaritons in the nanostructure.

\* \* \* \* \*

UNITED STATES PATENT AND TRADEMARK OFFICE
CERTIFICATE OF CORRECTION

PATENT NO. : 8,437,001 B2  
APPLICATION NO. : 13/157154  
DATED : May 7, 2013  
INVENTOR(S) : Cheng et al.

Page 1 of 1

It is certified that error appears in the above-identified patent and that said Letters Patent is hereby corrected as shown below:

In the Specifications:

In column 2 at line 26, Change "coaslescence" to --coalescence--.

In column 14 at lines 5-6, Change "microfludics" to --microfluidics--.

In column 14 at line 44, Change "10 μm. between" to --10 μm, between--.

In column 15 at line 13, Change "111-201," to --{11-20},--.

In the Claims:

In column 17 at line 2, In Claim 1, Change "shape;" to --shape; and--.

In column 17 at line 63, In Claim 11, Change "layer;" to --layer; and--.

In column 18 at line 55, In Claim 18, Change "eptaxial" to --epitaxial--.

Signed and Sealed this  
Fifteenth Day of October, 2013

Teresa Stanek Rea  
*Deputy Director of the United States Patent and Trademark Office*